(12) United States Patent
Polak

(10) Patent No.: US 9,731,129 B2
(45) Date of Patent: Aug. 15, 2017

(54) DEEP ELECTRODE INSERTION FITTING IN COCHLEAR IMPLANT PATIENTS WITH RESIDUAL HEARING

(71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/072,541

(22) Filed: Mar. 17, 2016

(65) Prior Publication Data

US 2016/0279412 A1    Sep. 29, 2016

(51) Int. Cl.
*A61N 1/36*    (2006.01)
*A61N 1/05*    (2006.01)
*H04R 25/00*   (2006.01)

(52) U.S. Cl.
CPC ....... *A61N 1/36032* (2013.01); *A61N 1/0541* (2013.01); *H04R 25/48* (2013.01); *H04R 25/502* (2013.01); *H04R 25/70* (2013.01)

(58) Field of Classification Search
CPC ............... A61N 1/36032; A61N 1/0541
USPC ........................................ 607/57
See application file for complete search history.

(56) References Cited

U.S. PATENT DOCUMENTS 4,617,913 A * 10/1986 Eddington ......... A61N 1/36032
                                                   607/57
8,000,798 B2    8/2011 Gantz et al.
2005/0203590 A1 * 9/2005 Zierhofer ............. H04R 25/505
                                                   607/57

(Continued)

FOREIGN PATENT DOCUMENTS

DE    102015104614   3/2015
WO    WO 96/34508    10/1996
WO    WO 01/19135    3/2001

OTHER PUBLICATIONS

International Searching Authority, German International Search Report for PCT/EP2016/056636, dated Jun. 22, 2016, 8 pages.

(Continued)

*Primary Examiner* — Paula J Stice
(74) *Attorney, Agent, or Firm* — Sunstein Kann Murphy & Timbers LLP

(57) ABSTRACT

A hearing signal processor processes an input sound signal and generates an electrical communications signal for an upper range of sound frequencies, and an acoustic communications signal for a lower range of sound frequencies. An implanted electrical stimulation subsystem includes an electrode array with one or more electrode contacts in an acoustically perceivable cochlear region retaining residual natural hearing. The electrical stimulation subsystem receives the electrical communications signal and delivers corresponding electrical stimulation signals to the electrode contacts for electrical stimulation of adjacent neural tissue. An external acoustic stimulation subsystem receives the acoustic communications signal and delivers corresponding amplified acoustic stimulation signals to the ear canal of the patient. The upper range and the lower range overlap and the electrical stimulation signals and the amplified acoustic stimulation signals are coordinated for simultaneous delivery to the acoustically perceivable cochlear region.

4 Claims, 6 Drawing Sheets

(56) References Cited

U.S. PATENT DOCUMENTS

| | | | |
|---|---|---|---|
| 2006/0287690 A1* | 12/2006 | Bouchataoui | H04R 25/606 607/57 |
| 2011/0077712 A1 | 3/2011 | Killian | |
| 2011/0230934 A1* | 9/2011 | Zierhofer | A61N 1/36032 607/57 |
| 2013/0116747 A1 | 5/2013 | Crawford et al. | |
| 2015/0032186 A1* | 1/2015 | Cushing | A61N 1/36032 607/57 |

OTHER PUBLICATIONS

Verbist, et al, "Consensus Panel on a Cochlear Coordinate System Applicable in Histologic, Physiologic and Radiologic Studies of Human Cochlea", *Otology & Neurotogy*, 31:722-370, 2010, 10 pages.

Kestner, "Cochlear-Implanta-Systeme", Schauenburg: Karin Kester Verlag, 2005. S. 9-1-1-9-910, http://www.kestner.de/n/verschiedenes/presse/2005/ImplKat_Cochlea-2005.pdf, 55 pages.

* cited by examiner

DEEP ELECTRODE INSERTION FITTING IN COCHLEAR IMPLANT PATIENTS WITH RESIDUAL HEARING

FIELD OF THE INVENTION

The present invention relates to hybrid electric acoustic (EAS) hearing systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

In some patients with some residual hearing in the lower acoustic frequencies, a conventional hearing aid and a cochlear implant can be combined together in a hybrid Electric Acoustic Stimulation (EAS) system. The hearing aid acoustically amplifies lower acoustic frequencies perceived by human ear, while the cochlear implant electrically stimulates the middle and high frequencies. See von Ilberg et al, *Electric-Acoustic Stimulation of the Auditory System*, ORL 61:334-340; Skarzynski et al, *Preservation of Low Frequency Hearing in Partial Deafness Cochlear Implantation (PDCI) Using the Round Window Surgical Approach*, Acta OtoLaryngol 2007; 127:41-48; Gantz & Turner, *Combining Acoustic and Electrical Speech Processing: Iowa/Nucleus Hybrid Implant*, Acta Otolaryngol 2004; 124:344-347; Gstottner et al., *Hearing Preservation in Cochlear Implantation for Electric Acoustic Stimulation*, Acta Otolaryngol 2004; 124:348-352; all incorporated herein by reference.

FIG. 1 also shows some components of a typical EAS system which includes an external microphone that provides an acoustic signal input to an external signal processor 111 where two different signal processing paths are developed. An upper acoustic frequency range communications signal containing middle and high frequency range acoustic is converted into a digital data format, such as a sequence of data frames, for transmission via a transmitter coil 107 over a corresponding implanted receiver coil 106 into the electric implant 108 (a typical cochlear implant system). Besides receiving the processed acoustic information, the electric implant 108 also performs additional signal processing such as error correction, pulse formation, etc., and produces an electric stimulation pattern (based on the extracted acoustic information) that is sent through an electrode lead 109 to an implanted electrode array 110. Typically, this electrode array 110 includes multiple electrode contacts on its outer surface that provide selective electric stimulation of the cochlea 104. The external signal processor 111 also creates a lower acoustic frequency range communications signal to a conventional hearing aid 105 in the ear canal which acoustically stimulates the tympanic membrane 102, and in turn the middle ear 103 and cochlea 104.

In some coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

FIG. 2 shows the major functional blocks in a typical cochlear implant signal processing system wherein band pass signals are processed and coding to generate electrode stimulation signals to stimulation electrodes in an implanted cochlear implant electrode array. For example, commercially available Digital Signal Processors (DSP) can be used to perform speech processing according to a 12-channel CIS approach. The initial acoustic audio signal input is produced by one or more sensing microphones, which may be omnidirectional and/or directional. Preprocessor Filter Bank 201 pre-processes the initial acoustic audio signal with a bank of multiple band pass filters, each of which is associated with a specific band of audio frequencies—for example, a digital filter bank having 12 digital Butterworth band pass filters of 6th order, Infinite Impulse Response (IIR) type—so that the acoustic audio signal is filtered into some N band pass signals, $B_1$ to $B_N$ where each signal corresponds to the band of frequencies for one of the band pass filters. Each output of the CIS band pass filters can roughly be regarded as a sinusoid at the center frequency of the band pass filter which is modulated by the envelope signal. This is due to the quality factor ($Q\approx 3$) of the filters. In case of a voiced speech segment, this envelope is approximately periodic, and the repetition rate is equal to the pitch frequency. Alternatively and without limitation, the Preprocessor Filter Bank 201 may be implemented based on use of a fast Fourier transform (FFT) or a short-time Fourier transform (STFT). Based on the tonotopic organization of the cochlea, each electrode contact in the scala tympani often is associated with a specific band pass filter of the external filter bank.

FIG. 3 shows an example of a short time period of an audio speech signal from a microphone, and FIG. 4 shows an acoustic microphone signal decomposed by band-pass filtering by a bank of filters into a set of signals. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety:

```
for j = 0 to number of channels - 1 do
    for s = 0 to number of samples - 1 do
        Y_j(s) = B_{0j} * X_j(s) + Z_{0j}
        for i = 0 to order - 3 do
            Z_{ij} = B_{i+1,j} * X_j(s) + Z_{i+1,j} - A_{i+1,j} * Y_j(s)
        end for
        Z_{order-2,j} = B_{order-1,j} * X_j(s) - A_{order-1,j} * Y_j(s)
    end for
end for
```

The band pass signals $B_1$ to $B_N$ (which can also be thought of as frequency channels) are input to a Signal Processor 202 which extracts signal specific stimulation information—e.g., envelope information, phase information, timing of requested stimulation events, etc.—into a set of N stimulation channel signals $S_1$ to $S_N$ that represent electrode specific requested stimulation events. For example, channel specific sampling sequences (CSSS) may be used as described in U.S. Pat. No. 6,594,525, which is incorporated herein by reference in its entirety. For example, the envelope extraction may be performed using 12 rectifiers and 12 digital Butterworth low pass filters of 2nd order, IIR-type.

A Pulse Generator 205 includes a Pulse Mapping Module 203 that applies a non-linear mapping function (typically logarithmic) to the amplitude of each band-pass envelope. This mapping function—for example, using instantaneous nonlinear compression of the envelope signal (map law)—typically is adapted to the needs of the individual cochlear implant user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_M$ that provide an optimal electric representation of the acoustic signal. A logarithmic function with a form-factor C typically may be applied as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals $A_1$ to $A_M$ outputs from the Pulse Mapping Module 203.

The Pulse Generator 205 also includes a Pulse Shaper 204 that develops the set of electrode stimulation signals $A_1$ to $A_M$ into a set of output electrode pulses $E_1$ to $E_M$ for the electrode contacts in the implanted electrode array which stimulate the adjacent nerve tissue. The electrode stimulation signals $A_1$ to $A_M$ may be symmetrical biphasic current pulses with amplitudes that are directly obtained from the compressed envelope signals.

In the specific case of a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

Another cochlear implant stimulation strategy that does transmit fine time structure information is the Fine Structure Processing (FSP) strategy by Med-El. Zero crossings of the band pass filtered time signals are tracked, and at each negative to positive zero crossing, a Channel Specific Sampling Sequence (CSSS) is started. Typically CSSS sequences are only applied on the first one or two most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

Many cochlear implant coding strategies use what is referred to as an N-of-M approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

One method to reduce the spectral clustering of stimulation per time frame is the MP3000™ coding strategy by Cochlear Ltd, which uses a spectral masking model on the electrode channels. Another method that inherently enhances coding of speech onsets is the ClearVoice™ coding strategy used by Advanced Bionics Corp, which selects electrode channels having a high signal to noise ratio. U.S. Patent Publication 2005/0203589 (which is incorporated herein by reference in its entirety) describes how to organize electrode channels into two or more groups per time frame. The decision which electrode channels to select is based on the amplitude of the signal envelopes.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc. But some stimulation arrangements are quite power consuming, especially when neighboring electrodes are used as current sinks. Up to 10 dB more charge might be required than with simple mono-polar stimulation concepts (if the power-consuming pulse shapes or stimulation modes are used continuously).

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties). According to the Greenwood scale, 360° of electrode insertion in the tonotopically organized cochlea covers the acoustic frequency region from 1 kHz and higher. See Greenwood, *A Cochlear Frequency-Position Function For Several Species 29 Years Later*, J Acoustic Soc Am, 1990; 87(6):2592-2605; incorporated herein by reference.

In a normal hearing ear, one frequency component consecutively stimulates multiple neural populations. This phenomenon was described as the "travelling wave" as shown in FIG. 5 from Von Békésy, Georg. *Experiments in hearing*. Ed. Ernest Glen Wever. Vol. 8. New York: McGraw-Hill, 1960 (incorporated herein by reference in its entirety). That is, in response to a pure tone, the basilar membrane resonates in a travelling wave (the ascending numbers within FIG. 5) which gradually grows in amplitude (the dashed lines in FIG. 5) as it moves along the cochlear duct from the stapes (base) toward the helicotrema (apex).

One quality of the travelling wave that is partly reflected in modern cochlear implant systems is that each frequency component reaches a peak amplitude at a specific spot within the cochlea (the tonotopic principle discussed above). These spectro-temporal properties can also be observed in the activity of cat's cochlear nerve fibres shown in FIG. 6 from Secker Walker et al, *Time domain analysis of auditory nerve fiber firing rates*, J Acoust Soc Am, 88(3), 1990, p. 1427-1436 (incorporated herein by reference in its entirety). FIG. 6 shows neural activity in the cochlear nerve over time at nerve fibres with different characteristic frequencies in response to synthetic vowels. One dominant frequency component in the synthetic vowel stimuli is the fundamental frequency (F0), which in FIG. 6 can be clearly identified as a regular pattern starting at high frequencies and ending several milliseconds later at low frequencies. The black curve in the shaded box in FIG. 6 indicates the frequency-specific time delays or the neural responses. Higher frequency components also can be observed between the F0 structures; for example, harmonics that are visible between 1800 and 1000 Hz. Similar to the F0 structures, they start at high frequency fibers and end some milliseconds later at low frequency fibers. This spectro-temporal excitation behaviour is not currently explicitly implemented in cochlear implant systems.

Loeb G., *Are cochlear implant patients suffering from perceptual dissonance*? Ear Hear, 26, 2005, p. 435-450 (incorporated herein by reference in its entirety) describes that phase-locking occurs over a substantial length of the cochlea. Furthermore, the action potentials exhibit a coherent spatial gradient with the steepest and most rapidly changing gradient of the phase occurring next to the place of the resonant frequency. At this point, the travelling wave starts to significantly slow down and dissipates. The phase gradient is believed to substantially contribute to pitch perception, especially in loud situations where harmonics are not resolved.

Existing coding approaches take into account some of the temporal properties of the acoustic signal. CIS determines frequency-specific envelopes which inherently contain a certain amount of information about individual low frequency components such as the fundamental frequency. More advanced approaches for calculating band specific envelopes also have been described; for example, U.S. Patent Publication 2006/0235486 (which is incorporated herein by reference in its entirety). The latter and CIS both sample the band pass envelopes with fixed rate stimulation pulses to resemble rudimentary properties of the basilar membrane movement. Other advanced systems as described in U.S. Patent Publication 2011/0230934 (which is incorporated herein by reference in its entirety) explicitly extract temporal characteristics of a band pass signal by identifying phase characteristics such as zero crossings. The described system triggers channel-specific sequences of stimulation pulses at each detected zero crossing. Each of the foregoing arrangements attributes certain frequency components to certain stimulation places. U.S. Patent Publication 2011/0230934 also explicitly takes into account the timing of certain frequency components.

Vocoder-based cochlear implant stimulation arrangements such as CIS and N-of-M do not take into account the travelling wave properties of normal acoustic hearing. The acoustic signal is analysed by filter banks or FFT and assigned either to single intracochlear electrodes, or to simultaneous stimulation of multiple adjacent electrodes. While filter banks can mimic the latencies of single frequency components at the place of stimulation, they are not able to mimic other aspects of the travelling wave behaviour such as the spectro-temporal distribution of this component to neighbouring stimulation sites, starting at a more basal site with low amplitude and ending at a more apical stimulation site with a maximum of stimulation at a site in between. An FFT, also used for mimicking the tonotopic principle in a cochlear implant is no better able to replicate the general latency differences between the frequency components (at the place of stimulation) nor does it provide the spectro-temporal behaviour described above.

In those patients receiving hearing implants who retain significant post-surgical residual natural hearing, typically, the residual hearing is in the lower frequency bands, which tonotopically corresponds to the deepest locations within the cochlea. In some cases, an apical portion of the implanted electrode array reaches far enough in to the cochlea to enter into the regions with residual hearing. In such cases, it has been suggested that the most apical electrode channels be turned off. For example, U.S. 2013/0116746 suggests that the electrode array be inserted only to a shallow depth in the scala tympani which typically is a region without residual hearing. Or if the most apical contacts of the electrode array actually are located in the acoustically perceivable region of the patient, to intentionally introduce a frequency gap between the acoustically perceivable frequencies and the electrically perceivable frequencies by turning off one or more of the most apical electrode contacts to create a (small) region without any hearing stimulation, either acoustic or electric.

U.S. Pat. No. 8,000,798 suggests an electrode array that after insertion has a subset of electrode contacts beyond a first basal turn of the cochlea, and activating one or more of the contacts in this subset while simultaneously allowing natural acoustic hearing to occur in one or more locations beyond the first basal turn. But it is apparent from the description that this patent describes "a relatively very thin and short electrode array that is insertable into the basal region of the cochlea and past the first turn thereof"

WO 00/69513 suggests a hybrid cochlear stimulation arrangement (i.e., combined electrical stimulation together with acoustic stimulation of residual hearing) that uses an electrode array which is no longer than 8 mm—shorter than the distance from the cochleostomy or round window membrane to the first basal turn.

All these existing measures are based on current beliefs that electrically stimulated hearing is different from natural acoustic hearing, and that electric stimulation interacts with acoustic hearing.

SUMMARY OF THE INVENTION

Embodiments of the present invention are directed to a signal processing arrangement and corresponding method for an electric acoustic stimulation (EAS) hearing system. A hearing signal processor is configured to process an input sound signal and generate: i. an electrical communications signal representative of an upper range of sound frequencies present in the input sound signal, and ii. an acoustic communications signal representative of a lower range of sound frequencies present in the input sound signal. An implanted electrical stimulation subsystem includes an electrode array having a plurality of electrode contacts implanted in a patient cochlea with one or more electrode contacts in an acoustically perceivable cochlear region retaining residual natural hearing. The electrical stimulation subsystem is configured to receive the electrical communications signal from the hearing signal processor and deliver corresponding electrical stimulation signals to the electrode contacts for electrical stimulation of adjacent neural tissue. An external acoustic stimulation subsystem is configured to receive the acoustic communications signal from the hearing signal processor and deliver corresponding amplified acoustic stimulation signals to the ear canal of the patient. The hearing signal processor is configured to overlap the upper range and the lower range and coordinate the electrical stimulation signals and the amplified acoustic stimulation signals for simultaneous delivery to the acoustically perceivable cochlear region.

In further specific embodiments, the electrical stimulation signals may be frequency specific sampling sequence (FSSS) and/or channel specific sampling sequence (CSSS) signals. The electrical stimulation signals also may be a patient-specific, frequency-specific function of stimulation location, rate, and level. The electrical stimulation signals for the one or more electrode contacts may include fine structure information. And the one or more electrode contacts in the acoustically perceivable cochlear region may be implanted at least 24 mm into the patient cochlea.

DETAILED DESCRIPTION OF SPECIFIC EMBODIMENTS

Frequency specific sampling sequence (FSSS) arrangements such as those descried in co-pending U.S. Provisional Patent Application Ser. No. 62/212,643, filed Sep. 1, 2015, and rate-location matched stimulation arrangements such as those descried in co-pending U.S. Provisional Patent Application 62/212,642, filed Sep. 1, 2015 and in from German Patent Application DE 102015104614, filed Mar. 26, 2015, can be particularly useful for patients with residual natural acoustic hearing who receive an EAS hybrid system. In such cases, a deeply inserted electrode array can be used which is inserted with the apical portion inside the acoustically functioning interior of the cochlea. This acoustically functioning portion of the cochlea that contains the electrode array is referred to as the "A region." Similarly, "deep insertion" in this context refers to electrode arrays having a length, for example, of 24-32 mm, where the latter length corresponds to complete cochlear coverage. Simultaneous acoustic and electric stimulation in the A region means that nerve signals are elicited in response to natural acoustic stimulation and also in response to the application of electrical pulses via the electrode contacts in the A region at the same time and at the same place.

Although the conventional wisdom is to avoid providing simultaneous acoustic stimulation and electric stimulation to an A region, the inventor has determined that under the right conditions such simultaneous stimulation may be beneficial. This kind of simultaneous stimulation previously has been avoided because of the inherent stimulation mismatch arising from the different natures of stimulation types. For example, natural acoustic stimulation is much more frequency selective than artificial electric stimulation with state-of-the-art speech coding strategies. Nevertheless it has surprisingly turned out that such simultaneous stimulation may be beneficial for the patient if:

There is a frequency match between the acoustic stimulation and the electrical stimulation. That is, the electrode contacts located in the A region are transferring information about the same sound frequencies as is the acoustic stimulation, where the match is as close as possible. An optimal or near-to-optimal electrical stimulation frequency may be derived from a postoperative CT scan to identify the exact location of the electrode contacts and adjust the stimulation frequencies on the contacts in the A region according to the Greenwood function (tonotopically); and complete fine structure information is present in the electrical stimulation. So if, for example, the A region is up to 500 Hz, then the fine structure is presented up to above 500 Hz for the assigned electrode channels.

Figure 5:
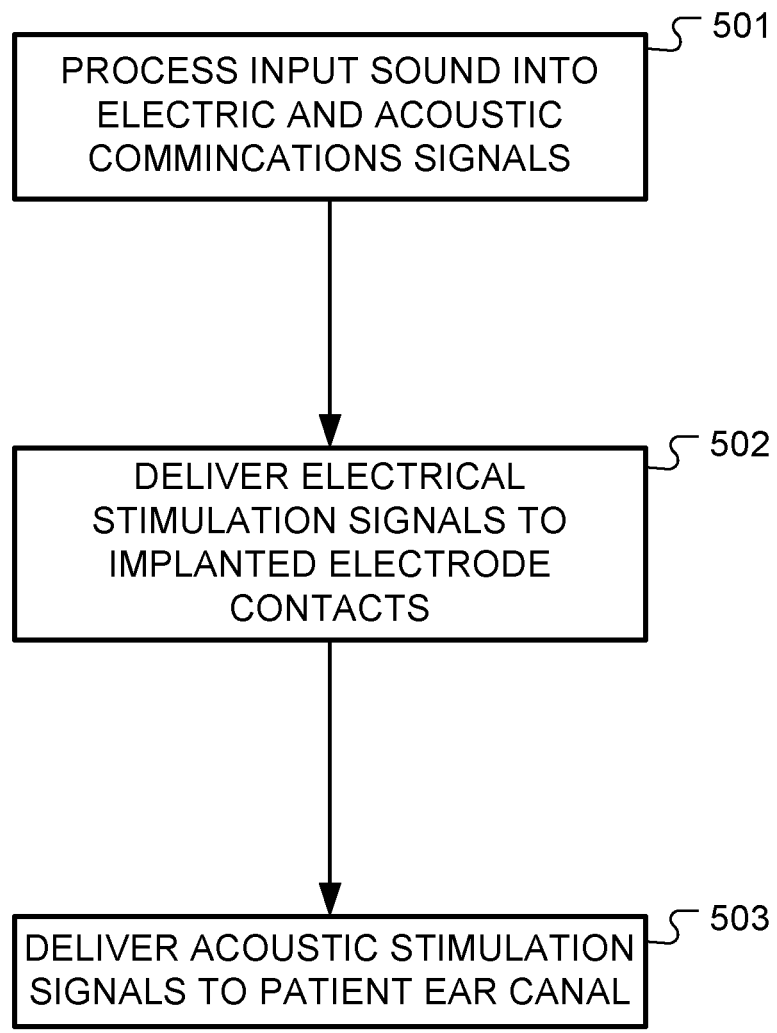
FIG. 5 shows various logical blocks in a process of combined electrical and acoustic stimulation according to an embodiment of the present invention.

FIG. 5 is a flow chart showing various logical steps in producing coordinated electrical and acoustic stimulation signals in an electric acoustic stimulation (EAS) hearing system according to an embodiment of the present invention. A pseudo code example of such a method can be set forth as:

```
Input Sound Processing:
    SignalFregRanges (input_sound, elec_upper, acoustic_lower)
Stimulation Signal Processing:
    ElecStim (elec_upper, elec_stim)
    AcousticStim (acoustic_lower, acoustic_stim)
```

Figure 6:
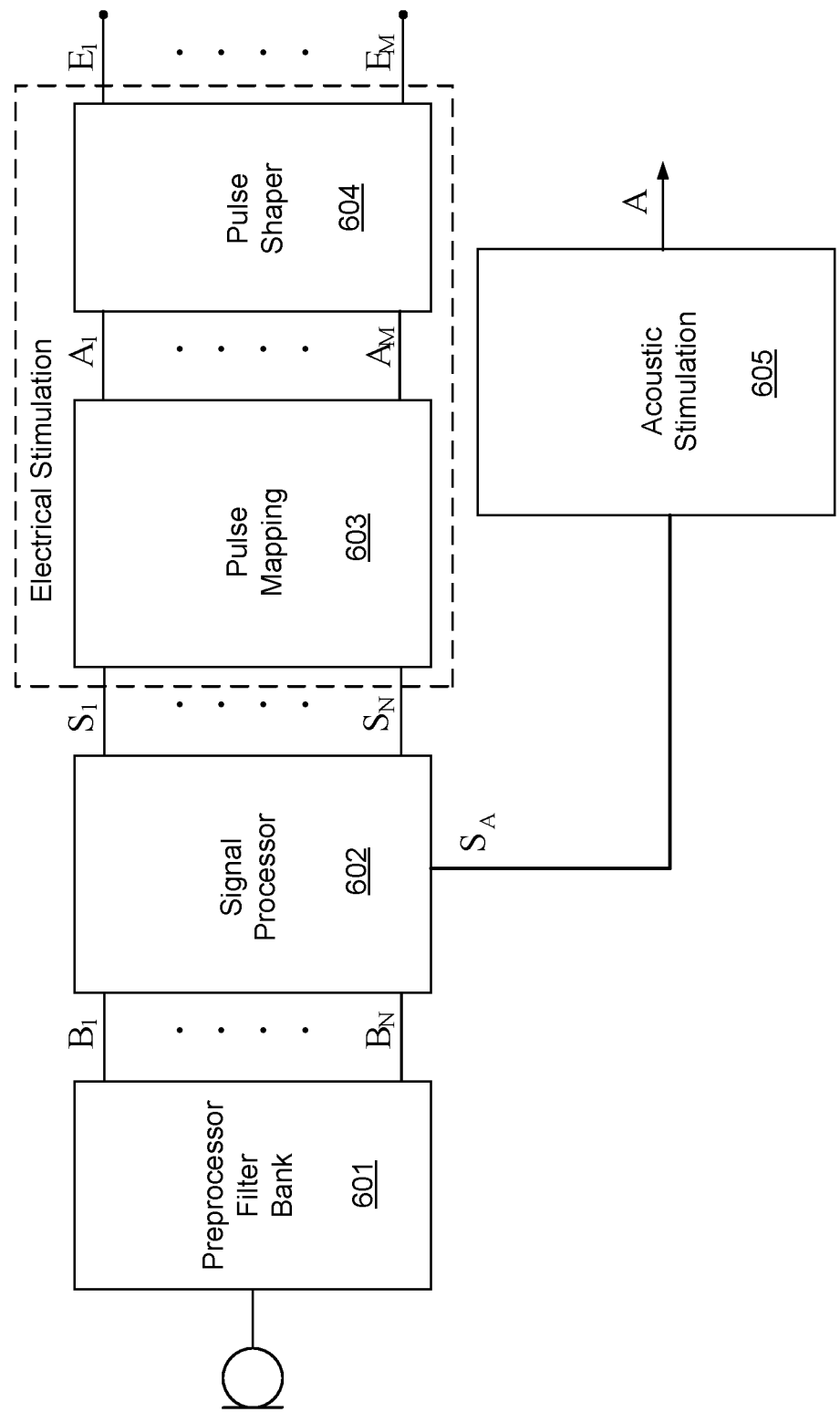
FIG. 6 shows various functional blocks in a combined electrical and acoustic stimulation system according to an embodiment of the present invention.

FIG. 6 shows various functional blocks in a combined electrical and acoustic stimulation system according to an embodiment of the present invention. The details of such an arrangement are set forth in the following discussion.

Figure 1:
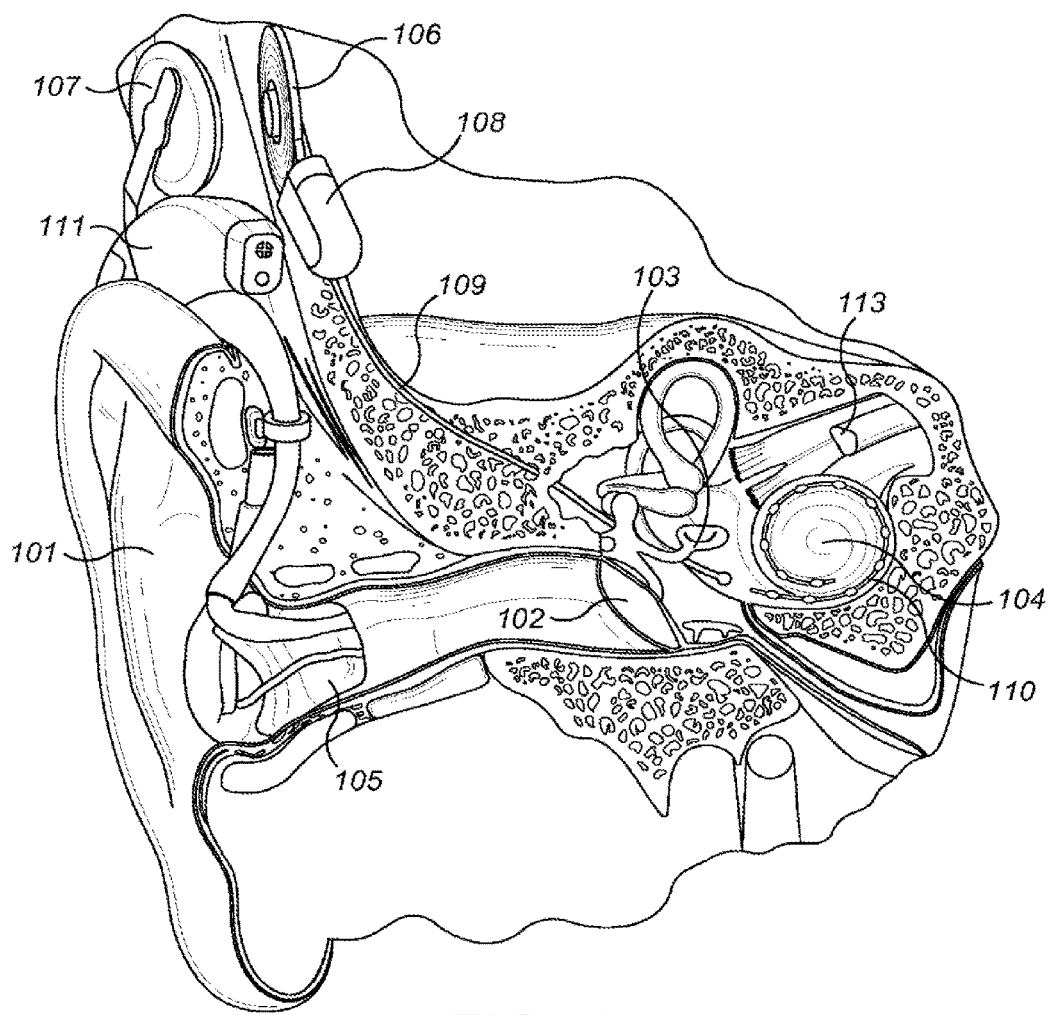
FIG. 1 shows a section view of a human ear with a typical cochlear implant system designed to deliver electrical stimulation to the inner ear.
Figure 2:
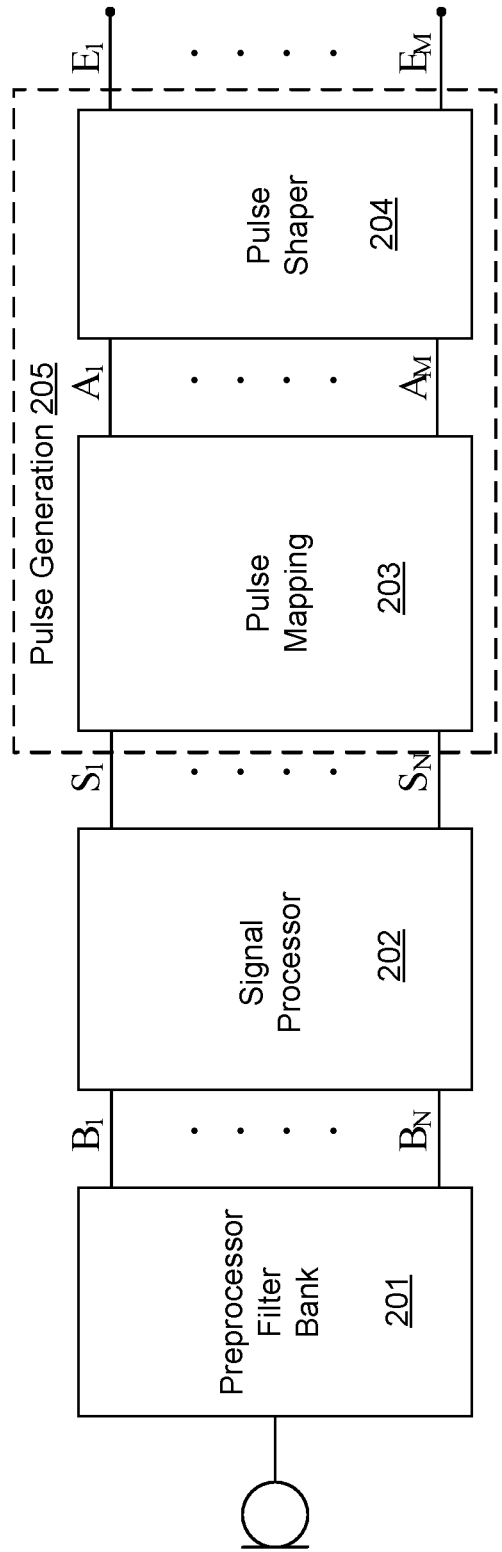
FIG. 2 shows various functional blocks in a continuous interleaved sampling (CIS) processing system.
Figure 3:
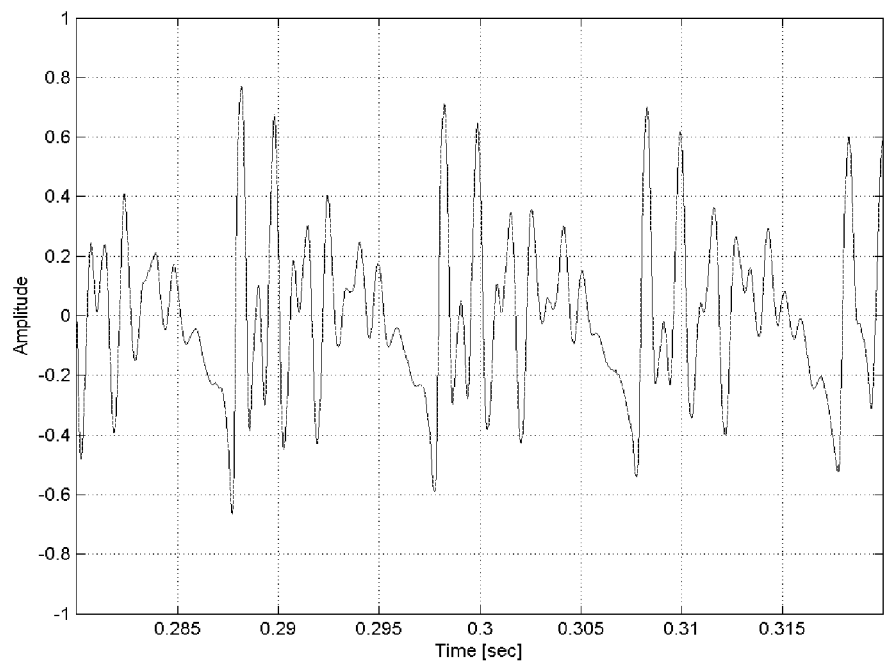
FIG. 3 shows an example of a short time period of an audio speech signal from a microphone.
Figure 4:
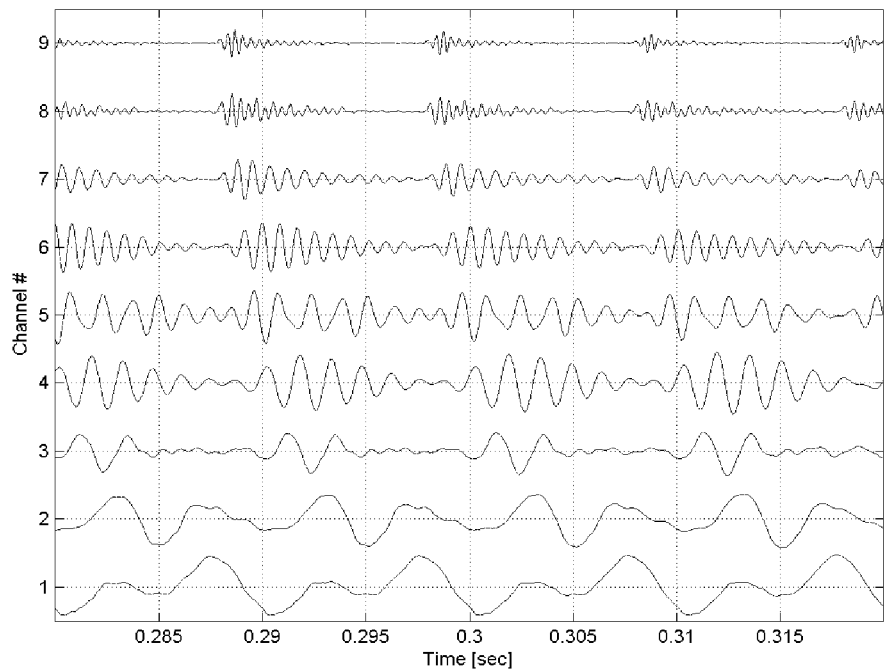
FIG. 4 shows an acoustic microphone signal decomposed by band-pass filtering by a bank of filters into a set of band pass signals.

As in the arrangement discussed above with respect to FIG. 2, a preprocessor signal filter bank 601 can be configured to decompose an input sound signal into band pass frequency component signals $B_1$ to $B_N$, step 501, representing an estimate of instantaneous input frequency/timing and component level/amplitude such that each band pass frequency component signal $B_1$ to $B_N$ changes over time in characteristic timing and amplitude. The timing of the band pass frequency component signals $B_1$ to $B_N$ typically may reflect frequency-specific response latencies and/or phase characteristics. The hearing signal processing module 602 then processes the band pass frequency component signals $B_1$ to $B_N$ to generate electrical communications signals $S_1$ to $S_N$ which are representative of an upper range of sound frequencies present in the input sound signal, and also an acoustic communications signal $S_A$ which is representative of a lower range of sound frequencies present in the input sound signal.

An implanted electrical stimulation subsystem includes a pulse mapping module 603 and a pulse shaper 604 as described above with respect to FIG. 2, which are configured to receive the electrical communications signals $S_1$ to $S_N$ from the hearing signal processor 602 and deliver corresponding electrical stimulation signals $E_1$ to $E_M$ to the electrode contacts for electrical stimulation of adjacent neural tissue, step 502. One or more of the electrode contacts towards the apical end of the electrode array is located in an acoustically perceivable cochlear region which retains some residual natural hearing. An external acoustic stimulation subsystem 605 is configured to receive the acoustic communications signal $S_A$ from the hearing signal processor 602 and deliver corresponding amplified acoustic stimulation signals A to the ear canal of the patient, step 503. The hearing signal processor 602 further is configured to overlap the upper range and the lower range and coordinate the electrical stimulation signals $E_1$ to $E_N$ and the amplified acoustic stimulation signals A for simultaneous delivery to the acoustically perceivable cochlear region.

As indicated above, the electrical stimulation signals $E_1$ to $E_M$ in specific embodiments may be FSSS and/or CSSS stimulation signals. For example, the length of the FSSS can vary based on the number of electrode channels and the number of the CSSS per channel. The lengths of the electrode channel CSSS per FSSS may be constant, however, varying CSSS lengths per FSSS also may be possible, such as longer CSSS at more apical channels or longer/shorter CSSS at the maximum level of the FSSS, etc. Some embodiments also may apply a Channel Interaction Compensation (CIC) algorithm (e.g., U.S. Pat. No. 7,917,224; incorporated herein by reference in its entirety) to the amplitudes of simultaneous FSSS to provide a desired loudness level to the user. The onset of the CSSS within a FSSS is controlled by the phase of the travelling wave. Subthreshold stimulation on individual electrode channels may be applied within a single FSSS in order to support and maintain spontaneous action potentials at the stimulation locations. Frequency specific characteristics of the FSSS such as amplitude shape, spread over electrode positions, and duration (of entire FSSS and channel specific CSSS per FSSS) can be stored as templates in system memory that is accessible to the hearing signal processing module 602.

Figure 7:
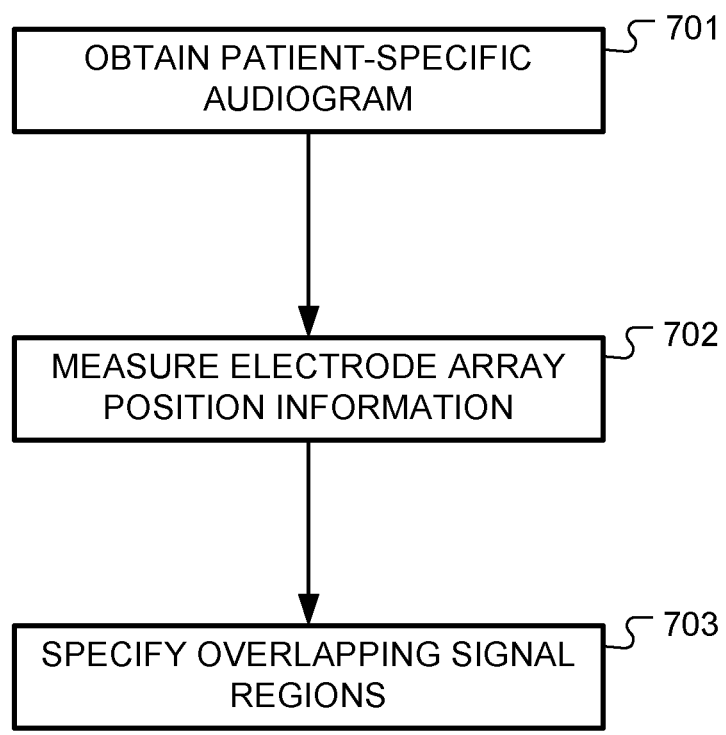
FIG. 7 shows various logical blocks in a process of fitting a combined electrical and acoustic stimulation system according to an embodiment of the present invention.

FIG. 7 shows various logical blocks in a process of fitting a combined electrical and acoustic stimulation system according to an embodiment of the present invention. The first steps in such a fitting process would involve obtaining a patient audiogram, step 701, and measuring information about the electrode position in the cochlea such as the electrode insertion angle, step 702. Then the acoustically perceivable cochlear region is determined, step 703, where one or more electrode contacts at the apical end of the inserted electrode array overlaps with the region of residual natural hearing; for example, by applying the Greenwood function to the electrode insertion angles. Then the electrode contacts in the acoustically perceivable cochlear region can be fit based on applying simultaneous electrical acoustic stimulation to those contacts. The remaining electrode contacts and the acoustic stimulation subsystem can be fit following known procedures. Rate-location matched stimulation may be applied on all channels independently of whether they are within the acoustic region or not.

Patients fitted as described above with simultaneous electrical and acoustic stimulation to an acoustically perceivable cochlear region may realize better sound perception in difficult conditions such as noise. In addition, the fitting procedure may actually take less time since there is no need to decide which electrode contacts have to be turned off. In addition, there is no need to change the electrical stimulation range when natural hearing changes (e.g. when the frequency range of natural hearing further decreases over time after implantation).

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of operating a electric acoustic stimulation (EAS) hearing system, the method comprising:
    for an implanted electrical stimulation subsystem having an electrode array implanted in a patient cochlea with a plurality of electrode contacts for delivering electrical stimulation signals to adjacent neural tissue, determining an overlap region in an acoustically perceivable cochlear region retaining residual natural hearing and containing one or more electrode contacts;
    pre-processing an input sound signal with a band pass filter bank to generate a plurality of representative band pass signals each associated with a specific band of audio frequencies;
    processing the plurality of band pass signals to generate:
        i. an electrical communications signal representative of an upper range of sound frequencies present in the input sound signal, and
        ii. an acoustic communications signal representative of a lower range of sound frequencies present in the input sound signal, wherein a portion of the upper range and the lower range overlap;
    receiving the electrical communications signal in the implanted electrical stimulation subsystem and delivering corresponding electrical stimulation signals to the electrode contacts; and
    receiving the acoustic communications signal in an external acoustic stimulation subsystem and delivering corresponding amplified acoustic stimulation signals to an ear canal of the patient;
    wherein the electrical stimulation signals and the amplified acoustic stimulation signals are coordinated for simultaneous delivery to the overlap region of acoustically perceivable cochlear region.

2. The method according to claim 1, wherein the electrical stimulation signals are channel specific sampling sequence (CSSS) signals.

3. The method according to claim 1, wherein the electrical stimulation signals are a patient-specific, frequency-specific function of stimulation location, rate, and level.

4. The method according to claim 1, wherein the electrical stimulation signals for the one or more electrode contacts include fine structure information.

* * * * *

UNITED STATES PATENT AND TRADEMARK OFFICE
CERTIFICATE OF CORRECTION

PATENT NO. : 9,731,129 B2
APPLICATION NO. : 15/072541
DATED : August 15, 2017
INVENTOR(S) : Marek Polak It is certified that error appears in the above-identified patent and that said Letters Patent is hereby corrected as shown below:

On the Title Page

Below Abstract, delete "4 Claims, 6 Drawing Sheets" and insert --5 Claims, 6 Drawing Sheets--

In the Claims

In Column 12, Line 32:
Insert --5. The method according to claim 1, wherein the one or more electrode contacts in the acoustically perceivable cochlear region are implanted at least 24 mm into the patient cochlea.--

Signed and Sealed this
Thirty-first Day of July, 2018

Andrei Iancu
*Director of the United States Patent and Trademark Office*